| United States Patent [19] | [11] Patent Number: 4,831,181 |
|---|---|
| Boesten et al. | [45] Date of Patent: May 16, 1989 |

[54] PROCESS FOR THE PREPARATION OF ASPARTYLPHENYLALANINE METHYL ESTER FROM N-FORMYLASPARTYLPHENYLALANINE METHYL ESTER

[75] Inventors: Wilhelmus H. J. Boesten, Sittard; Bernardus H. N. Dassen, Heerlen, both of Netherlands

[73] Assignee: Stamicarbon B.V., Geleen, Netherlands

[21] Appl. No.: 188,418

[22] Filed: Apr. 29, 1988

[30] Foreign Application Priority Data

May 1, 1987 [NL] Netherlands .......................... 8701035

[51] Int. Cl.$^4$ ............................................ C07C 101/02
[52] U.S. Cl. ....................................................... 560/41
[58] Field of Search ............................................ 560/41

[56] References Cited
FOREIGN PATENT DOCUMENTS 61-197593  9/1986  Japan ...................................... 560/41
1218907    1/1971  United Kingdom ................... 560/41
2144748    3/1985  United Kingdom ................... 560/41

*Primary Examiner*—Bruce D. Gray
*Attorney, Agent, or Firm*—Cushman, Darby & Cushman

[57] ABSTRACT

The invention relates to a process for the preparation of aspartylphenylalanine methyl ester from N-formylaspartylalanine methyl ester by treatment with an acid, characterized in that N-formylaspartylalanine methyl ester is treated at 30°-60° C. with at least 0.5 molar equivalent oxalic acid per mole of N-formylaspartylphenylalanine methyl ester in a solvent mixture in which N-formylaspartylphenylalanine methyl ester dissolves well and in which the oxalic acid salt of aspartylphenylalanine methyl ester is poorly soluble, after which the oxalic acid salt of aspartylphenylalanine methyl ester is removed by filtration, dissolved in water subsequently neutralized with the aid of an inorganic base with formation of free aspartylphenylalanine methyl ester.

9 Claims, No Drawings

PROCESS FOR THE PREPARATION OF ASPARTYLPHENYLALANINE METHYL ESTER FROM N-FORMYLASPARTYLPHENYLALANINE METHYL ESTER

The invention relates to a process for the preparation of aspartylphenylalanine methyl ester from N-formylaspartylphenyl-alanine methyl ester by treatment with an acid. The process is particularly suitable for the preparation of α-L-aspartyl-L-phenylalanine methyl ester. This substance, also termed aspartame, is a low-caloric intensive sweetener with excellent sweetening properties. Aspartame is used as a sweetener in food and drinks, as described in the American patent U.S. Pat. No. 3.492.131.

Aspartame is a dipeptide, in which both amino acids are in the L-form and the amino group in the aspartyl part is in position with respect to the peptide bond. Similar compounds in which one or both amino groups exist in the D-form, or in which the amino group is situated in β-position, have no sweetening properties and are therefore of no economic interest. For this reason it is important to couple the aspartic acid and the phenylalanine (methyl ester) in such a manner as to produce a maximum yield of α-L-aspartyl-L-phenylalanine (metyl ester). As is known, protective groups are used in the peptide synthesis for functional groups that do not partake in the formation of the peptide bond. The formyl group is a suitable N-protecting group, and is used as such in the synthesis of aspartame (see e.g. GB-A-8314907).

The removal of the N-protecting formyl group from the N-formylaspartylphenylalanine methyl ester formed is an essential step in the aspartame production process, which partly determines the yield of the process. This removal of formyl is generally considered a difficult step because the peptide bond and/or the ester group may be split at the same time as the N-formyl group and undesired side-reactions, such as the formation of diketopipe-razine or esterification of the free carboxyl group, may take place. Therefore it is desirable to minimize such side reactions in technical-scale implementations.

Various deformylation reactions are known from the literature (Houben Weyl 15-I, pp. 167-9). If applied to dipeptide derivatives such as N-formylaspartylphenylalanine methyl ester, the aforementioned side-reactions are unavoidable. GB-A-8314907 describes a process for the deformylation of α,β-N-formyl-L-aspartyl-L-phenylalanine methyl ester, in which the starting compound is treated with phosphoric acid and a lower alkyl alcohol in an organic solvent and in the presence of acetic acid. In repeating out this process (see comparative example 1), the applicant found that the results given in the aforementioned patent were not nearly obtained. JP-A-1197593 shows that treatment of α-N-formyl-L-aspartyl-L-phenylalanine with inorganic acids, such as hydro-chloric acid or sulphuric acid, or with organic acids, such as methanesulphonic acid or p-toluenesulphonic acid, in the presence of methanol, resulted in a high yield of α-L-aspartyl-L-phenyl-alanine dimethyl ester.

The aim of the invention is to find an economically attractive process for the deformylation of N-formylaspartylphenyl-alanine methyl ester under conditions at which the other func-tional groups in the compound hardly react and at which the formation of diketopiperazine is minimized.

Surprisingly, it has now been found that treatment of the starting compound with oxalic acid in a certain suitable solvent mixture results in a new and very simple process with practically no undesired side reactions.

The process according to the invention for the preparation of aspartylphenylalanine methyl ester from N-formylaspartylphenyl-alanine methyl ester by treatment with an acid is characterized in that N-formylaspartylalanine methyl ester is treated at 30°-60° C. with at least 0.5 molar equivalent oxalic acid per mole of N-formylaspartylphenylalanine methyl ester in a solvent mixture in which N-formylaspartylphenylalanine methyl ester easily dissolves and in which the oxalic acid salt of aspartylphenylalanine methyl ester is poorly soluble, after which the oxalic acid salt of aspartylphenylalanine methyl ester is separated by filtration, dissolved in water and subsequently neutralized with the aid of an inorganic base with formation of free aspartylphenylalanine methyl ester.

More in particular, the invention provides a process that can be used in the preparation of aspartame via N-formyl-L-α-aspartyl-L-phenylalanine methyl ester or a mixture of the α- and β-isomers of that compound. The process according to the inven-tion is even more surprising because much poorer results are obtained with other organic acids of comparable acidity.

The mild acidolysis of the process according to the invention prevents the splitting of the peptide bond and prevents saponification of the ester group and/or esterification of the free carboxyl group. Because the deformylated product precipitates with oxalic acid immediately after its formation, the formation of large quantities of the undesired diketopiperazine is also prevented. Analysis shows that the precipitate of aspartylphenylalanine methyl ester with oxalic acid consists of aspartylphenyl-alanine methyl ester and oxalic acid in a molar ratio of 2:1. A mixture of methyl isobutyl ketone and methanol in a volume-tric ratio of 3:1 to 11:1 is a very suitable solvent mixture. Preferably, methyl isobutyl ketone and methanol are mixed in a volumetric ratio of 6.5 to 7:1. At ratios lower than 3:1 too much of the oxalate formed remains in solution.

The concentration of the starting product to be deformylated in the solvent mixture is 0.1 to 0.5 mole per liter, preferably 0.3 to 0.35 mole per liter.

The oxalic acid is used in an amount of at least 0.5 molar equivalent per mole of N-formylaspartylphenylalanine methyl ester. The amount of oxalic acid need not be more than 2.2 molar equiva-lents with respect to the starting compound. Preferably, an amount of 1.0 to 1.5 molar equivalents of oxalic acid per mole of N-formylaspartylphenylalanine methyl ester is used.

The deformylation reaction is effected with stirring at a temperature of 30°-60° C., preferably 40°-50° C. For complete conver-sion of the starting material a reaction time of 50-100 hours is required.

The invention is elucidated with the following examples.

EXAMPLE I

At room temperature, 13.86 grams (=0.11 mole) of oxalic acid.2H2O was added to a suspension of 32.2 grams (=0.1 mole) of α-N-formyl-L-aspartyl-L-phenylalanine methyl ester in 258 ml of methyl isobutyl ketone and 37.5 ml of methanol. This reaction mixture was then maintained at 50° C., with constant stirring, for 66 hours and then cooled to 25° C. This caused crystallization of a solid, which was subsequently removed by filtration, washed with 100 ml of methyl isobutyl ketone and 100 ml of acetone and then dried. The yield amounted to 26.7 grams. HPLC analysis showed that 90.1% of the product consists of the oxalic acid salt of α-aspartame and 9.7% of diketopiperazine.

This corresponds to a yield of 0.071 mole of aspartame (as salt of oxalic acid) and 0.01 mole of diketopiperazine, respectively, on the basis of the N-formylaspartame used at the start.

EXAMPLE II

The process of example I was repeated, with the understanding that 0.11 mole of oxalic acid.2H2O was added to 0.1 mole of α-N-formyl-L-aspartyl-L-phenylalanine methyl ester in 258 ml of methyl isobutyl ketone and 37.5 ml of methanol. The reaction mixture was maintained at 40° C., with stirring, for 66 hours and subsequently cooled and processed. The yield amounted to 20.4 grams, consisting of 93.1% oxalate of α-aspartame and 2.5% diketopiperazine. This corresponds to a yield of 0.056 mole of aspartame (as salt of oxalic acid) and 0.002 mole of diketopiperazine, respectively, on the basis of the N-formylaspartame used at the start.

EXAMPLES III+IV

Experiments were carried out in the same way as in examples I and II. The reaction time was again 66 hours in each case, but now the process was effected at 45° C. (example III) and 55° C. (example IV), respectively.

|  | yield in grams | Consisting of (in %) | | yield in mole aspartame* | diketo- piperazine |
|---|---|---|---|---|---|
|  |  | oxalate | diketopi- perazine |  |  |
| Ex. III | 23.7 | 93.0 | 3.3 | 0.065 | 0.003 |
| Ex. IV | 25.4 | 85.4 | 11.2 | 0.064 | 0.011 |

*as salt of oxalic acid

EXAMPLE V

At room temperature, 30 grams of oxalic acid.2H2O was added to a suspension of 68 grams (=0.21 mole) of α,β-N-formyl-L-aspartyl-L-phenylalanine methyl ester (α:β=66:34) in 516 ml of methyl isobutyl ketone and 75 ml of methanol. The mixture was subsequently heated at 40° C. for 90 hours. Then the mixture was cooled, and the precipitate was removed by filtration and subsequently washed with 150 ml of methyl isobutyl ketone and 100 ml of acetone and dried. The yield was 42.2 grams.

This amount was introduced into 300 ml of water, after which the pH was raised from 2.1 to 5.2 with the help of concentrated ammonia. The mixture was then stirred for 3 hours at room temperature, after which the precipitate was removed by filtration, washed with a total of 300 ml of water and then dried. The product obtained weighed 22 grams and analysis showed that it contained:

72% α-aspartame
27.5% β-aspartame
<0.2% diketopiperazine
<0.1% α,β-L-aspartyl-L-phenylalanine
<0.1% α,β-N-formyl-L-aspartyl-L-phenylalanine methyl ester 295 ppm of oxalic acid.

COMPARATIVE EXAMPLE 1a (according to example III of GB-A-8314907)

22.7 ml of 85% aqueous phosphoric acid was added, at room temperature, to a solution of 32.2 grams of α,β-N-formyl-L-aspartyl-L-phenylalanine methyl ester (α:β=66:34) in 123 ml of ethyl acetate, 13 ml of acetic acid and 128 ml of methanol. The mixture was heated at 40° C. for 8 hours and then cooled.

It appeared to be difficult to filter the crystallized product. For this reason the precipitate obtained was completely dissolved in water (total weight of the solution 213,6 grams).

Analysis of the solution obtained showed that 0.014 mole of α-aspartame ends up in the 'precipitate' in the form of phosphate. In addition, the 'precipitate' appeared to contain α-aspartame (0.002 mole), as well as 0.001 mole of diketopiperazine.

Analysis showed that the filtrate contained 0.01 mole of α-aspartame (as phosphate), 0.005 mole of α-aspartame (as phosphate) and 0.002 mole of diketopiperazine, as well as non-deformylated product. It may be concluded that the deformylation reaction is far from completed after 8 hours.

COMPARATIVE EXAMPLE 1b 22.7 ml of 85% aqueous phosphoric acid was added, at room temperature, to a solution of 32.2 grams of α-N-formyl-L-aspartyl-L-phenylalanine methyl ester in 123 ml of ethyl acetate, 13 ml of acetic acid and 128 ml of methanol. The mixture was subse-quently maintained at 40° C. for 24 hours and then cooled to room temperature. This resulted in a precipitate of in total 19.9 grams that could be filtered without difficulty. Analysis showed that 85.3% of this precipitate consisted of the phosphoric acid salt of α-aspartame, 0.5% of diketopiperazine, 0.8% of L-α-aspartyl-L-phenylalanine and 0.9% of α-N-formyl-L-aspartyl-L-phenylalanine methyl ester. This corresponds to a yield of 43.3% α-aspartame (as salt of phosphoric acid).

COMPARATIVE EXAMPLE 2a 19.75 grams of benzenesulphonic acid (0.125 mole) was added, at room temperature, to a suspension of 32.2 grams of α-N-formyl-L-aspartyl-L-phenylalanine methyl ester in 258 ml of methyl isobutyl ketone and 37.5 ml of methanol. This reaction mixture was then maintained at 50° C. for 66 hours, with stirring, and subse-quently cooled to 25° C. No precipitate was formed. Nor was a precipitate obtained when 12.0 grams of maleic acid (0.11 mole) was added instead of benzenesulphonic acid and the reaction mixture was stirred for 40 hours at 45° C. and subsequently cooled to 25° C.

COMPARATIVE EXAMPLE 2b

At room temperature 29.4 ml of dichloroacetic acid (0.33 mole) and 5 ml of water were added to a suspension of 32.2 grams of α-N-formyl-L-aspartyl-L-phenylalanine methyl ester in 258 ml of methyl isobutyl ketone and 37.5 ml of methanol. This reaction mixture was then maintained at 50° C. for 46 hours, with stirring, and was then cooled to 25° C. The crystals formed were subsequently washed 4× with 25 ml of methyl isobutyl ketone and dried. The yield was 26.0 grams. Analysis showed that 95% of this product was diketropiperazine.

We claim:

1. Process for the preparation of aspartylphenylalanine methyl ester from N-formylaspartylalanine methyl ester by treatment with an acid, characterized in that N-formylaspartylalanine methyl ester is treated at 30°–60° C. with at least 0.5 molar equivalent oxalic acid per mole of N-formylaspartylphenyl-alanine methyl ester in a solvent mixture in which N-formyl-aspartylphenylalanine methyl ester dissolves well and in which the oxalic acid salt of aspartylphenylalanine methyl ester is poorly soluble, after which the oxalic acid salt of aspartylphenylalanine methyl ester is removed by filtration with the aid of an inorganic base with formation of free aspartylphenylalanine methyl ester.

2. Process according to claim 1, in which N-formyl-L-α-aspartyl-L-phenylalanine methyl ester or a mixture of the α- and β-isomers of N-formyl-L-aspartyl-L-phenylalanine methylester is used as N-formylaspartylalanine methyl ester and the N-deformylated compound is aspartame or a mixture of α- and β-aspartame.

3. Process according to claim 1, characterized in that 1.0–2.2 molar equivalents oxalic acid per mole of N-formylaspartylphenylalanine methyl ester are used in the treatment with oxalic acid.

4. Process according to claim 3, characterized in that 1.0–1.5 molar equivalents oxalic acid per mole of N-formylaspartyl-phenylalanine methyl ester are used in the treatment with oxalic acid.

5. Process according to claim 1, characterized in that a combination of methyl isobutyl ketone and methanol in a volumetric ratio from 3:1 to 11:1 is used as solvent mixture for the treatment with oxalic acid and that the N-formylated starting compound amounts to 0.1 to 0.5 mole per liter.

6. Process according to claim 5, characterized in that the volumetric ratio of methyl isobutyl ketone and methanol is 6.5 to 7:1 and that the N-formylated starting compound amounts to 0.3 to 0.35 mole per liter.

7. Process according to claim 1, characterized in that the treatment with oxalic acid is effected at a temperature of 30°–60° C. for 24 to 72 hours.

8. Process according to claim 7, characterized in that the treatment with oxalic acid is effected at a temperature of 40°–50° C. for 24 to 72 hours.

9. Oxalic acid salt of aspartylphenylalanine methyl ester.

* * * * *

UNITED STATES PATENT AND TRADEMARK OFFICE
CERTIFICATE OF CORRECTION

PATENT NO.  : 4,831,181

DATED       : May 16, 1989

INVENTOR(S) : BOESTEN et al.

It is certified that error appears in the above-identified patent and that said Letters Patent is hereby corrected as shown below:

Column 1, line 19, please correct "in position" to read --in α position--;
column 1, line 33, please change "GB-A-8314907" to --GB-A-2140805--;
column 1, line 42, delete a hyphen in "diketopiperazine";
column 1, line 58, "JP-A-1197593" should be --JP-A-61197593--;
column 1, line 68, delete a hyphen in "functional";
column 2, line 9, delete a hyphen in "formylaspartylphenylalanine";
column 2, lines 10 and 11, "N-formylaspartylalanine" should be --N-formylaspartylphenylalanine--;
column 2, lines 37 and 38, delete a second hyphen in "aspartylphenylalanine";
column 2, line 40, delete a hyphen in "volumetric";
column 2, line 57, delete a hyphen in "conversion";
column 4, line 17, please change "α-aspartame" to --β-aspartame--;
column 4, lines 20 and 21, please change "0.005 mole of α-aspartame" to --0.005 mole of β-aspartame--;
column 4, line 31, delete a hyphen in "subsequently";
column 4, line 50, delete a hyphen in "subsequently";
column 4, lines 67 and 68, please correct the spelling of "diketopiperazine".

Signed and Sealed this

Twelfth Day of December, 1989

Attest:

JEFFREY M. SAMUELS

Attesting Officer        Acting Commissioner of Patents and Trademarks